(12) United States Patent
Just

(10) Patent No.: US 11,114,187 B1
(45) Date of Patent: Sep. 7, 2021

(54) SYSTEM AND METHOD FOR MANAGING OPERATING DATA FOR A MEDICAL ENVIRONMENT

(71) Applicant: Matthew Just, Duluth, MN (US)

(72) Inventor: Matthew Just, Duluth, MN (US)

(*) Notice: Subject to any disclaimer, the term of this patent is extended or adjusted under 35 U.S.C. 154(b) by 212 days.

(21) Appl. No.: 16/151,071

(22) Filed: Oct. 3, 2018

Related U.S. Application Data

(60) Provisional application No. 62/568,368, filed on Oct. 5, 2017.

(51) Int. Cl.
*G16H 10/60* (2018.01)
*G16H 80/00* (2018.01)
*G16H 40/20* (2018.01)

(52) U.S. Cl.
CPC ............ *G16H 10/60* (2018.01); *G16H 40/20* (2018.01); *G16H 80/00* (2018.01)

(58) Field of Classification Search
CPC ......... G16H 10/60; G16H 40/20; G16H 80/00
USPC ............................................................ 705/3
See application file for complete search history.

(56) References Cited

U.S. PATENT DOCUMENTS

| | | | | |
|---|---|---|---|---|
| 2005/0229110 A1* | 10/2005 | Gegner | .................. | G16H 40/63 715/800 |
| 2008/0312973 A2* | 12/2008 | Rosow | .................. | G06Q 40/08 705/5 |
| 2014/0372518 A1* | 12/2014 | Moore | .................... | G06F 9/451 709/203 |

FOREIGN PATENT DOCUMENTS

WO  WO-2008103509 A1 *  8/2008  ............. G16H 10/60

OTHER PUBLICATIONS

Beria D; A hybrid solution for a telecare system server, 2011 6th IEEE International Symposium on Applied Computational Intelligence and Informatics (SACI) (pp. 589-592) (Year: 2011).*

* cited by examiner

*Primary Examiner* — Hiep V Nguyen
(74) *Attorney, Agent, or Firm* — Uradnik Law Firm PC

(57) ABSTRACT

Disclosed herein are systems and methods of generating and displaying health-related information to a user, the health-related information being associated with a desired medical operating environment and/or a particular healthcare operating environment and/or an individual such as a patient, caregiver, staff member, etc.

9 Claims, 1 Drawing Sheet

SYSTEM AND METHOD FOR MANAGING OPERATING DATA FOR A MEDICAL ENVIRONMENT

RELATED APPLICATIONS

This application is related to and claims priority from U.S. provisional patent application Ser. No. 62/568,368 filed Oct. 5, 2017, entitled System and Method for Managing Operating Data for a Medical Environment, which is hereby incorporated by reference herein for all purposes.

FIELD OF THE DISCLOSURE

The invention relates generally to systems and methods for managing data associated with an medical operating environment, and more specifically to a system and method for maintaining information associated with the operation of a skilled nursing facility (e.g., hospital, nursing home, clinic, assisted living facility, etc.).

BACKGROUND

Medical operating environments often include numerous patients, providers, caregivers, etc. A large amount of data may be associated with the treatment of any one patient. Thus, for a medical operating environment having multiple patients, patient rooms, care providers, etc. considerable data must be tracked and reported. This task can be extremely cumbersome if performed manually. Accordingly, a new and improved system and method for tracking and reporting medical environmental data is needed.

SUMMARY

In one embodiment, a server system may be provided. At the server, one or more sources of operating data may be provided. One or more medical environments to which the operating data may relate may be located remotely from the server. Embedded within the server may be a local controller. Associated with a medical environment may be a remote controller. The local controller and the remote controller may be configured to communicate with each other, with the ability to transfer data between the server (at a source of operating data) and the environment (at the remote controller).

Data may be transferred between the server and the remote controller via a web connection such as the internet. The connection between the server and a remote controller may be wired or wireless, either in whole or in part. Data may be transferred via the connection using either standard or custom data transmission protocols.

At a medical environment, a remote controller may be embedded in a device such as a smartphone, a tablet, a computer, etc. The device may be used by an operator at the medical environment to create or modify a source of operating data. The source of operating data may be a database, from which one or more data files or data packages may be selected by an operator using a remote controller. Each data file or data package at least includes identifying information for its respective environment. In one embodiment, a data file or data package also may include unique identifying information for an individual associated with the environment.

Software code, such as an application or app, may be on the remote controller, the local controller, or both. The software code may provide the interface for the entry or the modification of operating data in a data file or data package. The software code may also provide a functional interface to an operator for retrieving operating data and presenting such data in the form of one or more received operating data reports.

In one embodiment, a received operating data report may include a graphic representation of all or a portion of a medical environment. The graphic representation may be a diagram, map, floorplan, etc. The graphic representation may include one or more symbols, icons, or other indicators to communicate a particular location within the environment and/or operating data of interest to an operator or user.

Other benefits and advantages of the present disclosure will be appreciated from the following detailed description.

DESCRIPTION OF THE DRAWINGS

Exemplary embodiments of an exemplary system and method in accordance with the disclosure herein are shown in the accompanying drawings.

DETAILED DESCRIPTION

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to information tracking and reporting; etc. Such aspects related to this disclosure do not depart from the invention, and it is therefore intended that the invention not be limited by the certain aspects set forth of the events and circumstances related to this disclosure.

Figure 2:
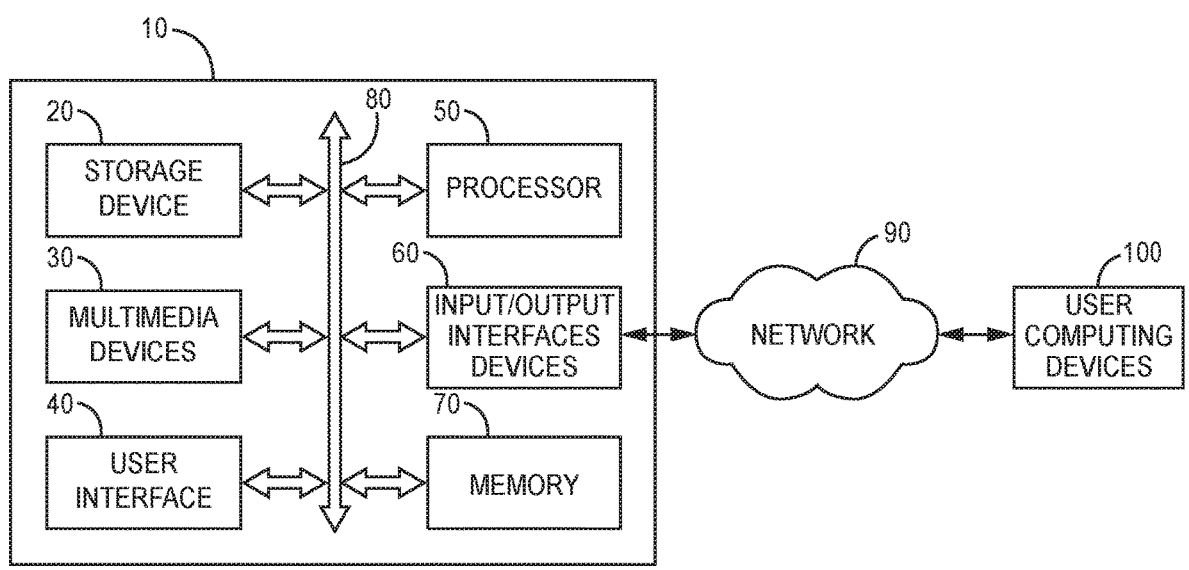
FIG. 2 is a block diagram illustrating one exemplary embodiment of a server system that may be used to implement certain systems and methods discussed herein.

As shown in FIG. 2, a server system 10 may include a database stored in a storage device 20, the database having information related to one or more medical operating environments 200. In one embodiment, the server 10 is located remotely from the medical operating environments 200.

A local controller associated with the medical operating environment 200 may be used to populate the database with one or more data files. Related data files may be linked by a common entry identification.

The local controller may be used to access a data entry interface. The data entry interface may have the ability to receive data for transfer to the server 10. The data entry interface may take any of a number of forms, e.g., radio buttons, drop-down menus, text entry fields, etc.

When entering information about a new or potential infection, for example, staff may be presented with a number of choices for infection types: urinary tract infection (UTI), skin and soft tissue infection (SSTI), respiratory infection, gastrointestinal infection, or other. Selection of a particular type results in prompts for the entry of data corresponding to the infection type. In this way, data files are created including attributes which may be later accessed for modification or use (e.g., in providing patient care, in the generation of medical operating environment reports, etc.).

Upon entry of a data file, a report may be generated for the data file. The report may be provided to a physician or other caregiver, prompting a response based on the information in the report. The response may be entered into the database as a related attribute. In one embodiment, the response may amount to instructions for care of a patient. Such instructions may then be reported to other caregivers to direct their actions for a particular patient.

Reports also may be generated for a particular embodiment that track data across a medical operating environment. In that way, items such as infection rates for a particular medical operating environment may be ascertained.

Figure 1:
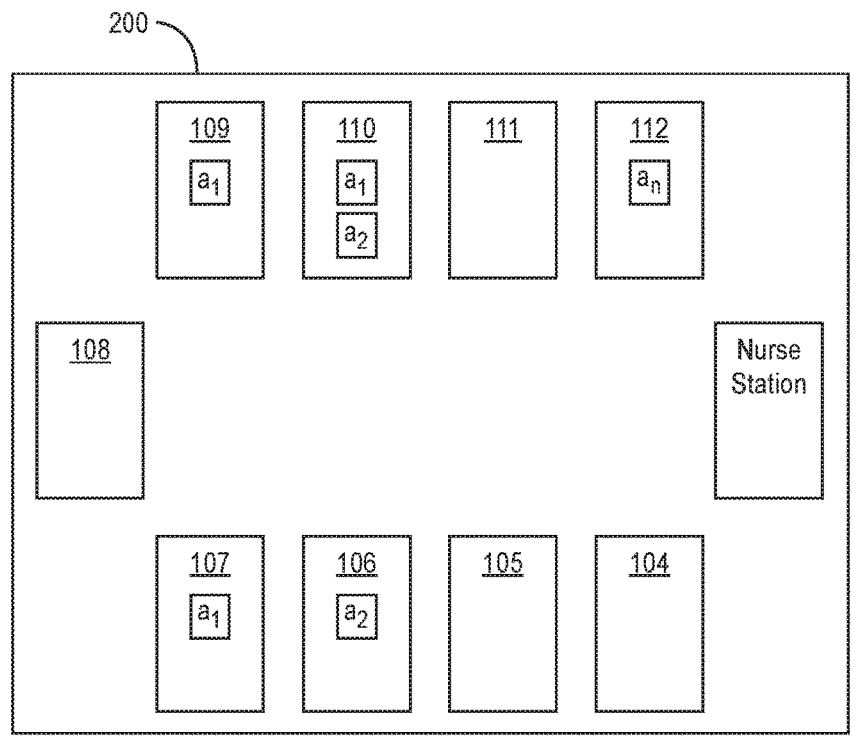
FIG. 1 is an exemplary embodiment of a graphic representation of an medical operating environment showing (by way of example only) various health-related attributes $a_1, a_2, \ldots, a_n$ associated with specific healthcare operating environments.

The forms in which data may be tracked are numerous, and thus may be tailored specifically for a given medical operating environment. A Situation, Background, Assessment, Recommendation (SBAR) approach may be followed. Some data file/response examples follow, and an exemplary graphical report is shown in FIG. 1. Each piece of information shown or described may be considered an attribute of a medical operating environment, healthcare operating environment, patient, etc. Of course, including as attributes specific bacteria types, as well as information associated for respiratory and other infections, are equally within the scope of the disclosure herein. Thus, the following are provided by way of example only.

Antibiotic Tracking Data

A data file related to antibiotic tracking may include the following types of data: entry identification (e.g., using a random number generator to provide an entry identification using the patient initials as the first two digits); date entered; patient name; patient date of birth; patient room number; nurse/staff entering information; medication ordered; route; dose; frequency of administration; therapy duration; prophylactic antibiotic (yes/no); diagnosis; and prescriber.

SSTI Formation Tracking Data

A data file related to SSTI formation tracking may include the following types of data: patient initials; entry identification (e.g., using a random number generator to provide an entry identification using the patient initials as the first two digits); nurse/staff entering information; provider name (MD, PA, CNP); room number of patient; patient on dialysis (yes/no); gender; age; weight; height; serum creatinine (mg/dL); blood pressure (systolic/diastolic); heart rate (beats per minute); respiratory rate (respirations per minute); temperature; patient have diabetes (yes/no); patient history of skin infections (yes/no); patient have medication allergies (yes/no); patient on Warfarin, Coumadin, or Jantoven (yes/no); patient antibiotic use in the last 14 days (yes/no); medication; dose; route of administration (PO, IV, IM); frequency of administration; duration of therapy; whether the patient displays fever of 100° F. (38° C.) or repeated temperatures of 99° F. (37° C.), redness, pain/tenderness, warmth, swelling (new or increasing), or pus at a wound, skin or soft tissue site (new or increasing); and other related information.

Provider Response on SBAR Form Tracking Data

A data file related to a provider response to an SBAR form may include the following types of data: nurse/staff entering information; provider responses/orders (e.g., assess vital signs; notify physician/PA/CNP if symptoms worsen or unresolved; for discomfort or prior to cleaning/dressing changes consider using paracetamol (or acetaminophen), an analgesic drug (APAP) per standing orders; provider did not respond; patient discharged/in hospital); antibiotic prescribed (yes/no); date prescribed; medication prescribed; medication dose; route of administration; frequency of administration; duration; diagnosis of SSTI (e.g., cellulitis, impetigo, other); location infection acquired (e.g., CAI (community acquired infection), HAI (hospital acquired infection), NHAI (nursing home acquired infection), other nosocomial (acquired in a different healthcare setting), unknown); and provider prescribing medication.

Staff Illness Tracking Data

A data file related to staff illness tracking may include the following types of data: entry identification; date entered; staff name; staff department; nurse/staff entering information; onset date; symptoms; whether staff member received medical treatment; whether an antibiotic or antiviral was prescribed to the staff member (yes/no); and other comments.

Staff-Chosen Antibiotic Tracking Data

A data file related to tracking a staff-chosen antibiotic may include the following types of data: employee entering information; patient initials; entry identification (e.g., random number generator used to provide entry ID using the patient initials as the first two digits); date of antibiotic start; room number of patient in facility; medication (antibiotic) ordered; route of administration (e.g., oral, IV, IM); dose of antibiotic; frequency of administration; duration of therapy; whether antibiotic is long term or prophylactic agent; diagnosis for antibiotic (e.g., UTI, cellulitis, impetigo, C-diff, sinusitis, pneumonia, bronchitis, other); where infection was acquired (e.g., CAI (community acquired infection), HAI (hospital acquired infection), NHAI (nursing home acquired infection), other nosocomial (acquired in another healthcare setting), or unknown); location prescribed (e.g., nursing home, hospital, emergency department, medical office); and prescriber's name.

UTI (No Catheter) Tracking Data

A data file related to tracking a urinary tract infection (UTI) where the patient is not using a catheter may include the following types of data: patient initials; entry identification (e.g., random number generator used to provide entry ID using the patient initials as the first two digits; nurse/staff entering information; provider name (MD, PA, CNP); whether the patient is on dialysis (yes/no); gender; age; serum creatinine; patient weight; patient height; patient room number; blood pressure (systolic/diastolic); heart rate; respiratory rate (in respirations per minute); temperature; whether the patient has diabetes (yes/no); whether the patient has medication allergies; whether the patient is on Warfarin, Coumadin, or Jantoven (yes/no); whether antibiotic use in the last 14 days (yes/no); medication; dose; route of administration; frequency of administration; duration of therapy; s/s of patient (e.g., acute dysuria alone; single temperature of 100° F. (38° C.) and at least one new or worsening of urinary urgency, urinary frequency, back or flank pain, suprapubic pain, gross hematuria, and urinary incontinence; no fever but two or more of the following new or worsening of urinary urgency, urinary frequency, back or flank pain, gross hematuria, urinary incontinence); and other information.

UTI (with Catheter) Tracking Data

A data file related to tracking a urinary tract infection where the patient is using a catheter may include the following types of data: patient initials; entry identification (e.g., random number generator used to provide entry ID using the patient initials as the first two digits); nurse/staff entering information; provider name (MD, PA, CNP); whether the patient is on dialysis (yes/no); gender; age; serum creatinine; weight; height; patient room number; blood pressure (systolic/diastolic); heart rate; respiratory rate; temperature; whether the patient has diabetes (yes/no); whether the patient has medication allergies (yes/no); whether the patient is on Warfarin, Coumadin, or Jantoven (yes/no); whether there has been antibiotic use in the last 14 days (yes/no); medication; dose; route of administration; frequency of administration; duration of therapy; whether the patient displays: Fever of more that 100° F. (38° C.), back or flank pain, acute pain, rigors/shaking chills or new onset delirium/dramatic change in condition; and other information.

UTI Provider Response Tracking Data

A data file related to tracking a urinary tract infection provider response may include the following types of data: Nurse/staff entering information; provider responses/orders (e.g., ordered UA/UC, encourage fluids, record fluid intake, assess vital signs, notify physician/PA/CNP if symptoms worsen or unresolved, provider did not respond, patient discharged/in hospital); whether an antibiotic was prescribed (yes/no); date prescribed; medication prescribed; dose of medication; route of administration; frequency of administration; therapy duration; diagnosis of UTI; where the infection was acquired (e.g., CAI (community acquired infection), HAI (hospital acquired infection), NHAI (nursing home acquired infection), other nosocomial (acquired in a different healthcare setting), unknown); provider prescribing the medication; and other information.

In one embodiment, a server computing system 10 may be provided for providing health-related information to a user, the server computing system 10 comprising a database storing health-related information for a number of patients; a non-transitory computer readable storage device 20 configured to store software instructions; a computer processor 50 configured to execute the software instructions to serve a website or mobile application content including user interface content renderable on a user computing device 100, wherein the user interface content comprises dynamic user interface controls for receiving identification information for a first patient associated with a first healthcare operating environment; presenting a first category of healthcare-related information for the first patient associated with the first healthcare operating environment and for a second patient associated with a second healthcare operating environment proximate the first healthcare operating environment, the first category of healthcare-related information comprising healthcare attributes of the first healthcare operating environment and the second healthcare operating environment; communicate the website or mobile application content to the user computing device 100, wherein the user computing device 100 renders the website or mobile application content to display the user interface content; receive the identification information for the first patient associated with the first healthcare operating environment, wherein the identification information for the first patient associated with the first healthcare operating environment is inputted via the dynamic user interface controls on the user computing device 100; access from the database attributes of the first healthcare operating environment and the second healthcare operating environment based on the identification information for the first patient associated with the first healthcare operating environment; serve an updated website or mobile application content including updated user interface content including a graphic indication of the first healthcare operating environment, the second healthcare operating environment, and the database attributes of the first healthcare operating environment and the second healthcare operating environment; and communicate the updated website or mobile application content to the user computing device 100, wherein the updated website or mobile application content is renderable by the user computing device 100 to display the updated user interface content.

Examples of a user computing device 100 are a desktop computer workstation, a smart phone, a computer laptop, a tablet PC, or any other similar device. The user computing device 100 in some embodiments may include a touchscreen that allows input to the device using one or more fingers or a stylus on a display screen. The user computing device 100 may comprise storage systems such as a hard drive or memory or other non-transitory data storage medium. The storage systems may be configured to store executable instructions that may be executed by one or more processors to perform computerized operations such as accepting data input from a user, providing output to a user using a display, etc.

One or more user computing devices may be in contact with a server 10 via a network 90, which may include any combination of networks, e.g., local area, wide area, Internet, ethernet LAN, cable modem, 802.11 access point, cell phone network, etc. The network 90 allows electronic transmissions between the server 10 and user computing devices 100.

The server 10 may comprise one or more servers and/or personal computers. The server may include a memory 70, which may include a random access memory for temporary information storage, a storage device 20 including a read only memory for permanent information storage, a hard drive, diskette, optical media storage device, flash drive, etc. The server 10 typically may include a standards-based bus system 80 for communication between various server modules, e.g., input/output interfaces or devices 60, display devices 40, multimedia devices 30, memory 70, mass storage devices 20, processing units 50, etc.

In accordance with one embodiment, a method for providing health-related information to a user comprises the steps of: (a) serving a website or mobile application content including user interface content renderable on a user computing device, wherein the user interface content comprises dynamic user interface controls for receiving identification information for a patient; (b) communicating the website or mobile application content to the user computing device, wherein the user computing device renders the website or mobile application content to display the user interface content; (c) receiving the identification information for the patient, wherein the identification information for the patient is inputted via the dynamic user interface controls of the user computing device; (d) accessing from a database health-related attributes of the patient; (e) serving an updated website or mobile application content including updated user interface content including the health-related attributes of the patient; and (f) communicating the updated website or mobile application content to the user computing device, wherein the updated website or mobile application content is renderable by the user computing device to display the updated user interface content. In one embodiment, the updated user interface content may include a graphic display of a first healthcare operating environment selected based on the identification information for the patient. The graphic display may include health-related attributes of the patient. In another embodiment, the graphic display or another report form may include calculated trend data based upon the health-related attributes of the patient. In the graphic display, in one embodiment health-related attributes of the patient may be color-coded. Further, the health-related attributes of the patient may include data in one or more of the following data categories described herein: antibiotic tracking data, SSTI formation tracking data, provider response on SBAR form tracking data, staff illness tracking data, staff-chosen antibiotic tracking data, UTI (no catheter) tracking data, UTI (with catheter) tracking data, UTI provider response tracking data.

FIG. 1 shows an exemplary graphic display for a medical operating environment 200 including multiple healthcare operating environments 104, 105, . . . , 112.

The healthcare operating environments 104, 105, . . . , 112 may indicate an associated health-related attribute $a_1, a_2, \ldots, a_n$. An individual patient also may be associated with a particular healthcare operating environment.

In one embodiment, a graphic display of a medical operating environment may be created using a digitized floorplan of the facility. Div tags (<div>) may be used to divide the floorplan into particular sections for particular data or function in the webpage or mobile application content. Attributes, then, may be applied in one or more layers corresponding to their respective sections. Of course, other ways of creating a digital image also may be used to create the graphic display.

In one embodiment, all health-related attributes for a particular set of patients or healthcare operating environments may be displayed. In another embodiment, one or more categories of health-related attributes may be selected by a user to be hidden from view, i.e., not shown. In another embodiment, health-related attributes are hidden from view until such time as for as long as a user hovers over a particular healthcare operating environment with a cursor, a touch, or similar indicator of location, at which point the information may be displayed to the user for such environment. In another embodiment, health-related attributes may be displayed for a medical operating environment in the order in which particular events occurred. In this way, for example, a dynamic presentation or display is made that can show (by way of example only) the spread of an infection across multiple healthcare operating environments and across a facility.

In another embodiment, health-related attributes may be used to determine whether the criteria for an infection is met for one or more patients. The server system or user computing device may cross-reference Loeb's criteria with patient signs and symptoms. Thus, additional data representing the percentages of infections that met criteria may be provided. Also, data representing inappropriate prescribing (i.e., prescription provided when infection criteria not met) may be presented.

In another embodiment, health-related attributes may be used to determine and identify potential reoccurring infections. By way of example only, patients may be identified who have had multiple antibiotics within a particular time period (e.g., within the last week, month, fourteen days, etc.). Also, a prediction of future resistance to prescribed antibiotics based upon past medication use may be provided.

In one embodiment, for a particular medical operating environment, attributes may be used to create and provide an antibiogram. The antibiogram is an overall profile of antimicrobial susceptibility testing results of a specific microorganism to a battery of antimicrobial drugs. Antibiograms help guide clinicians, pharmacists, and skilled nursing facilities in selecting the best empiric antimicrobial treatment in the event of pending microbiology culture and susceptibility results. An antibiogram provides an idea of what types of antibiotic resistance to be on the lookout for in a medical operating environment, and can improve an ability to avoid suboptimal therapies and in turn provide better care. It may also assist in identifying overuse of specific antibiotics, as more antibiotic use leads to more antibiotic resistance.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of examples and described in detail herein. However, it should be understood that the invention is not intended to be limited to the particular forms disclosed. Rather, the invention is to cover all modifications, equivalents and alternatives falling within the spirit and scope of the invention.

What is claimed is:

1. A server computing system for providing health-related information to a user, the server computing system comprising:
   a database storing health-related information for a number of patients;
   a non-transitory computer readable storage device configured to store software instructions;
   a computer processor configured to execute the software instructions to:
      serve a website or mobile application content including user interface content renderable on a user computing device, wherein the user interface content comprises dynamic user interface controls for
   receiving identification information for a first patient associated with a first healthcare operating environment;
   presenting together a first category of healthcare-related information for the first patient associated with the first healthcare operating environment and for a second patient associated with a second healthcare operating environment, the first category of healthcare-related information comprising healthcare attributes of the first healthcare operating environment and the second healthcare operating environment;

communicate the website or mobile application content to the user computing device, wherein the user computing device renders the website or mobile application content to display the user interface content;

receive the identification information for the first patient associated with the first healthcare operating environment, wherein the identification information for the first patient associated with the first healthcare operating environment is inputted via the dynamic user interface controls on the user computing device;

access from the database together attributes of the first healthcare operating environment and the second healthcare operating environment based on the identification information for the first patient associated with the first healthcare operating environment;

serve an updated website or mobile application content including updated user interface content including:

a graphic indication on a diagram, map, or floorplan of the first healthcare operating environment, the second healthcare operating environment, and the database attributes of the first healthcare operating environment and the second healthcare operating environment; and communicate the updated website or mobile application content to the user computing device, wherein the updated website or mobile application content is renderable by the user computing device to display the updated user interface content.

2. The server computing system of claim 1, wherein the computer processor is further configured to execute software instructions to provide updated user interface content including calculated trend data for the database attributes of the first healthcare operating environment.

3. The server computing system of claim 1, wherein the computer processor is further configured to execute software instructions to provide updated user interface content including database attributes of the first healthcare operating environment including data in one or more of the following data categories: antibiotic tracking data, SSTI formation tracking data, provider response on SBAR form tracking data, staff illness tracking data, staff-chosen antibiotic tracking data, UTI (no catheter) tracking data, UTI (with catheter) tracking data, UTI provider response tracking data.

4. A method for providing health-related information to a user, the method comprising:

serving a website or mobile application content including user interface content renderable on a user computing device, wherein the user interface content comprises dynamic user interface controls for receiving identification information for a patient;

communicating the website or mobile application content to the user computing device, wherein the user computing device renders the website or mobile application content to display the user interface content;

receiving the identification information for the patient, wherein the identification information for the patient is inputted via the dynamic user interface controls of the user computing device;

accessing from a database together attributes of a first healthcare operating environment and a second healthcare operating environment based upon health-related attributes of the patient;

serving an updated website or mobile application content including updated user interface content including together the attributes of a first healthcare operating environment and a second healthcare operating environment based upon health-related attributes of the patient; and communicating the updated website or mobile application content to the user computing device, wherein the updated website or mobile application content is renderable by the user computing device to display the updated user interface content including health-related attributes of the patient graphically indicated on a diagram, map, or floorplan.

5. The method of claim 4 wherein the updated user interface content includes a graphic display on a diagram, map, or floorplan of a first healthcare operating environment selected based on the identification information for the patient.

6. The method of claim 5 wherein the graphic display on a diagram, map, or floorplan includes the health-related attributes of the patient.

7. The method of claim 5 wherein the graphic display on a diagram, map, or floorplan includes calculated trend data based upon the health-related attributes of the patient.

8. The method of claim 4 wherein the health-related attributes of the patient are color-coded.

9. The method of claim 4 wherein the health-related attributes of the patient include data in one or more of the following data categories: antibiotic tracking data, SSTI formation tracking data, provider response on SBAR form tracking data, staff illness tracking data, staff-chosen antibiotic tracking data, UTI (no catheter) tracking data, UTI (with catheter) tracking data, UTI provider response tracking data.

* * * * *